United States Patent [19]

Ives

[11] 4,281,004
[45] Jul. 28, 1981

[54] PHENYLGUANIDINE THERAPEUTIC AGENTS

[75] Inventor: Jeffrey L. Ives, King of Prussia, Pa.

[73] Assignee: Pfizer Inc., New York, N.Y.

[21] Appl. No.: 135,374

[22] Filed: Mar. 31, 1980

[51] Int. Cl.$^3$ .................... A61K 31/44; C07D 401/12; C07D 405/12; A61K 31/40

[52] U.S. Cl. .................................... 424/263; 424/274; 424/275; 424/285; 546/281; 546/306; 546/332; 549/65; 260/326.85; 260/347.7

[58] Field of Search ...................... 546/281, 332, 306; 549/65; 260/347.7, 326.85; 424/263, 274, 275, 285

[56] References Cited

U.S. PATENT DOCUMENTS 4,101,659   7/1978   Rasmussen ...................... 424/248.56

FOREIGN PATENT DOCUMENTS 2272645 12/1975 France ................................ 260/326.85

*Primary Examiner*—Alan L. Rotman
*Attorney, Agent, or Firm*—Francis X. Murphy; Charles J. Knuth; Peter C. Richardson

[57] ABSTRACT

A series of phenylguanidine base compounds and their pharmaceutically acceptable acid addition salts have been found to be active as oral hypoglycemic agents. Preferred member compounds include N,N'-diphenyl-1-pyrrolidinocarboxamidine, N-phenyl-N'-methyl-N'-phenyl-1-pyrrolidinocarboxamidine and N-phenyl-N'-(p-chlorophenyl)-1-pyrrolidinocarboxamidine, and their hydrohalide acid addition salts. Synthetic routes leading to these compounds are described.

5 Claims, No Drawings

PHENYLGUANIDINE THERAPEUTIC AGENTS

BACKGROUND OF THE INVENTION

This invention relates to new and useful phenylguanidine hypoglycemic agents. More particularly, it is concerned with a series of phenylguanidine base compounds and their pharmaceutically acceptable acid addition salts, which are useful in therapy as oral hypoglycemic agents for the treatment of diabetes. The invention also includes various novel oral pharmaceutical compositions as well as a method of therapy.

In the past, various attempts have been made by numerous investigators in the specialized field of synthetic organic medicinal chemistry to obtain new and better oral hypoglycemic agents. For the most part, these efforts have principally involved the synthesis and testing of various heretofore new and unavailable organic compounds, particularly in the area of the sulfonylureas, in an endeavor to determine their ability to lower blood sugar (i.e., glucose) levels when given by the orgal route of administration. However, in the search for new and still more effective antidiabetic agents, far less is known about the effect of non-sulfonylureas and this is particularly so in the case of various phenylguanidine derivatives. For instance, the closest prior art is French Pat. No. 2,272,645 which discloses certain phenylguanidine compounds to be useful in the pharmaceutical field as antiarrhythmic agents and as diuretics (without any suggestion that they might also be useful for antidiabetic purposes).

SUMMARY OF THE INVENTION

In accordance with the present invention, it has now been rather surprisingly found that certain phenylguanidine derivatives are useful when employed in therapy as oral hypoglycemic agents for the treatment of diabetic subjects. More particularly, the novel method of treatment of the present invention involves treating a diabetic host by administering to said host an effective blood sugar lowering amount of a compound selected from the group consisting of phenylguanidine bases of the formula:

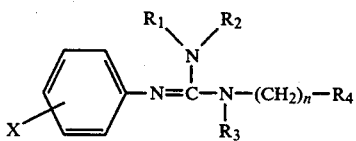

and the pharmaceutically acceptable acid addition salts thereof, wherein X is a member selected from the group consisting of hydrogen, fluorine, chlorine, bromine, trifluoromethyl, lower alkyl and lower alkoxy (each having from one to four carbon atoms); $R_1$ and $R_2$, when taken separately, are each lower alkyl, and when taken together complete a ring chosen from the group consisting of pyrrolidino, piperidino, homopiperidino, morpholino, thiomorpholino, piperazino, N-(lower alkyl)piperazino, N-benzylpiperazino and N-phenylpiperazino; $R_3$ is hydrogen or lower alkyl; $R_4$ is a member selected from the group consisting of phenyl, pyridyl, furyl, thienyl, 2-thiazolyl, 2-imidazolyl, 2-imidazolinyl and mono- and di-substituted phenyl wherein each substituent is chosen from the group consisting of fluorine, chlorine, bromine, trifluoromethyl, lower alkyl and lower alkoxy; and n is an integer of from zero to four, inclusive. These compounds are all useful in lowering blood sugar levels when given by the oral route of administration, i.e., they are useful as oral hypoglycemic agents.

The novel compounds of this invention are those phenylguanidines of formula I where $R_4$ is other than phenyl or mono- and di-substituted phenyl, i.e., they comprise those phenylguanidine bases of the formula:

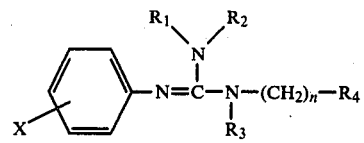

and the pharmaceutically acceptable acid addition salts thereof, wherein X is a member selected from the group consisting of hydrogen, fluorine, chlorine, bromine, trifluoromethyl, lower alkyl and lower alkoxy; $R_1$ and $R_2$, when taken separately, are each lower alkyl, and when taken together complete a ring chosen from the group consisting of pyrrolidino, piperidino, homopiperidino, morpholino, thiomorpholino, piperazino, N-(lower alkyl)piperazino, N-benzylpiperazino and N-phenylpiperazino; $R_3$ is hydrogen or lower alkyl; $R_4$ is a member selected from the group consisting of pyridyl, furyl, thienyl, 2-thiazolyl, 2-imidazolyl and 2-imidazolinyl; and n is an integer of from zero to four, inclusive.

Of especial interest in this connection are such typical and preferred member compounds of the invention as N,N'-diphenyl-1-pyrrolidinocarboxamidine, N-phenyl-N'-(p-chlorophenyl)-1-pyrrolidinocarboxamidine, N-phenyl-N'-(2,4-dichlorophenyl)-1-pyrrolidinocarboxamidine, N-phenyl-N'-methyl-N'-phenyl-1-pyrrolidinocarboxamidine, N-phenyl-N'-benzyl-1-pyrrolidinocarboxamidine, N-phenyl-N'-(2-pyridyl)-1-pyrrolidinocarboxamidine and N-phenyl-N'-(2-furfuryl)-1-pyrrolidinocarboxamidine, and their pharmaceutically acceptable acid addition salts, such as the hydrochlorides and hydriodides, for example. These particular compounds are all highly potent as regards their hypoglycemic activity (i.e., they exhibit a marked improvement in glucose tolerance). The preferred N'-(2-pyridyl) and N'-(2-furfuryl) derivatives are, as previously indicated, new compounds.

DETAILED DESCRIPTION OF THE INVENTION

In accordance with the process employed for preparing the compounds of this invention, an appropriately substituted haloamidine compound of the formula:

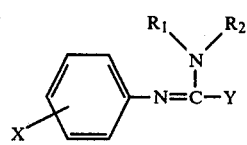

is reacted with a suitable amine of the formula $R_4(CH_2)_nNHR_3$, wherein X, $R_1$, $R_2$, $R_3$ and $R_4$ and n are all as previously defined and Y is halogen, preferably either chlorine or bromine. The desired final product is always obtained in the form of the corresponding hydrohalide salt. This particular reaction is normally conducted in a reaction-inert organic solvent at a temperature that is in the range of from about 0° C. up to about 50° C. for a period of about one to 24 hours. Preferred reaction-inert organic solvents for use in this connection include acetonitrile, lower dialkyl ethers like diethyl ether and diisopropyl ether, cyclic ethers such as tetrahydrofuran and dioxane and aromatic hydrocarbon solvents such as benzene, toluene, xylene and the like. Upon completion of the reaction, the desired product is then easily recovered by any number of conventional means and preferably by evaporating the solvent from the reaction mixture, followed by trituration of the residue with acetone or another similar organic solvent to give the hydrohalide salt in crystalline form.

The starting materials required for the reaction process of this invention are either well known compounds, like the aforesaid amines, or else they are easily prepared by those skilled in the art from more readily available materials using conventional methods of organic chemistry. For instance, the aforementioned haloamidine compounds are best prepared by reacting an appropriate isocyanide dihalide of the formula $RNC(Y)_2$, where R is phenyl or substituted phenyl as previously defined, with a corresponding amine of the formula $R_1R_2NH$. This particular reaction is generally carried out in a solvent of the same type as that employed in the production of the final products hereinbefore described and at a temperature that is in the range of from about $-25°$ C. up to about 35° C. The preferred reaction temperature is from about 0° C. to about 25° C. Further, the reaction is expeditiously conducted in the presence of an organic base such as a teritary amine, like a trialkylamine having from one to four carbon atoms in each alkyl group and preferably, triethylamine. In general, it is only necessary to employ a sufficient amount of base to effect removal of the hydrohalide byproduct and this would normally entail the use of at least about one mole equivalent of base with respect to one mole of dihalo isocyanide starting material and one mole equivalent of the secondary amine ($R_1R_2NH$) reagent. Upon completion of the reaction, the desired haloamidine compound can easily be isolated from the reaction mixture by any number of conventional procedures well known to those skilled in the art but, in practice, it is usually preferable to omit this step and use the reaction solution containing said intermediate directly in the next reaction step to form the desired phenylguanidine final product as previously described.

An alternate and equally facile route to the production of the phenylguanidine compounds of this invention involves treating the corresponding S-(lower alkyl-)isothiouronium salt of the formula:

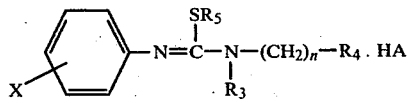

with an appropriate amine of the formula $R_1R_2NH$, where X, $R_1$, $R_2$, $R_3$ and $R_4$ and n are all as previously defined and $R_5$ is lower alkyl, and preferably alkyl having from one to three carbon atoms, while A represents the appropriate anion which is preferably bisulfate ($HSO_4^-$) or lower alkyl sulfate ($R_5SO_4^-$) or a halide ion such as bromide or iodide (most preferably, iodide). This particular reaction is normally carried out in a reaction-inert polar solvent medium at a temperature ranging from about 20° C. up to about 100° C. for a period of about four to about 96 hours and most conveniently, at a temperature ranging from about 25° C. to about 60° C. for from about four to about 72 hours. In practice, it is generally most convenient to heat the two reactants together under reflux in the polar solvent, employing substantially equimolar amounts of starting materials for this purpose, although a slight excess of one or the other is not harmful in this respect. Preferred reaction-inert polar solvents for use in this connection include water, lower alkanols such as methanol, ethanol, isopropanol and tert-butanol, etc., and lower N,N-di(lower alkyl)alkanoamides such as N,N-dimethylformamide, N,N-dimethylacetamide, N,N-diethylformamide, N,N-diethylacetamide, N,N-di(n-propyl)formamide and N,N-dimethylpropionamide, as well as mixtures of either of these two aforementioned type organic solvents with water. Upon completion of the reaction, the solvent is removed by means of conventional procedures and the resulting residue is then taken up in a suitable solvent system, such as one of the aforementioned types, from which it can be suitably crystallized. Alternatively, the product may separate first from the reaction mixture either during the course of the reaction itself or immediately thereafter, or it may be crystallized from the final reaction solution after some early initial concentration of same. In any event, the desired final product is thus obtained in the form of its crystalline acid addition salt by means of this particular reaction.

The starting materials required for the alternate reaction process of this invention are either well known compounds or else they are easily prepared by those skilled in the art in accordance with standard organic procedures. For instance, the aforementioned S-alkyl isothiouronium salts, which are sometimes called 2-alkyl-2-thiopseudoureas, are all members of a well known class of organic compounds and have been used as reagents before in this same general type of reaction, viz., the so-called "guanidine-forming" reaction. More specifically, they can be prepared by the reaction of an appropriate isothiocyanate of the formula $RN=C=S$, where R is phenyl or substituted phenyl as previously defined, with a corresponding amine of the formula $R_4(CH_2)_nNHR_3$ to form the desired intermediate product, viz., the corresponding thiourea compound of formula $RNHC(=S)N(R_3)(CH_2)_nR_4$ where R, $R_3$, $R_4$ and n are all as previously defined. This particular reaction is normally carried out in a polar organic solvent such as a lower alkanol like methanol, ethanol or isopropanol, etc., at a temperature ranging from about 0° C. up to about 40° C., although in practice it is usually most convenient to conduct the reaction at ambient temperatures. The substituted thiourea compound so obtained is then subsequently reacted with the appropriate alkylating agent of choice ($R_5A$) and preferably with a lower alkyl halide having from one to three carbon atoms in the alkyl moiety where the halide atom is either a bromide or an iodide. The most preferred reagent in this connection is methyl iodide. The alkylation reaction is best effected at the reflux temperature of the reaction mixture and this normally entails the use of a suitable organic solvent, such as a lower alkanol having from one to three carbon atoms and most preferably, methanol. In this way, the desired pseudothiourea is readily obtained in the form of its acid addition salt.

Still another method which can be used to prepared the phenylguanidine compounds of this invention involves first treating the aforementioned substituted thiourea compound of the formula $RNHC(=S)N(R_3)(CH_2)_nR_4$ with triphenylphosphine and carbon tetrachloride in the presence of an organic base, such as a tertiary amine like triethylamine. This particular reaction is usually conducted in an organic solvent medium, preferably using a halogenated hydrocarbon solvent such as methylene chloride for these purposes. The reaction is most conveniently carried out at the reflux point of the reaction mixture and the resulting chloroamidine intermediate is then purified by conventional means prior to use in the next step, which involves treatment with an appropriate amine $(R_1R_2NH)$. The latter reaction simply entails heating the two reactants together in a suitable organic solvent, such as a lower alkanol containing up to five carbon atoms, or any other polar organic solvent like tetrahydrofuran, dioxane, N,N-dimethylformamide, N,N-dimethylacetamide, etc., at a temperature ranging from about 35° C. up to about 75° C. for a period of about five to about 96 hours. Upon completion of the reaction, the cooled, spent reaction mixture is filtered and subsequently triturated with an excess of dilute aqueous acid to form the desired acid addition salt of the phenylguanidine final product so produced.

As a matter of fact, in each of the three principal synthetic methods described above, the phenylguanidine final products of this invention are always obtained in the form of an appropriate acid addition salt. However, the corresponding free base compounds can be readily prepared from the salts by merely using appropriate conventional procedures, for example, by treatment with an excess of aqueous alkali, followed by extraction of the aqueous mixture with a suitable organic solvent, such as a water-immiscible halogenated hydrocarbon solvent like dichloromethane or chloroform, etc. In this way, the desired free base compound is readily obtained and available for pharmaceutical use as such or for conversion to still other acid addition salts.

The pharmaceutically acceptable acid addition salts of the phenylguanidine base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt product is readily obtained.

As previously indicated, the phenylguanidine compounds of this invention are all readily adapted to therapeutic use as oral hypoglycemic agents, in view of their ability to lower the blood sugar levels of both diabetic and non-diabetic subjects to a substantially significant degree. For instance, N-phenyl-N'-methyl-N'-phenyl-1-pyrrolidinocarboxamidine as the hydrochloride salt, a typical and preferred agent of the present invention, has been found to consistently lower blood sugar levels in the fasted, glucose-loaded rat to a statistically significant degree when given by the intraperitoneal route of administration at a dose level of 50 mg./kg. without showing any substantial signs of toxic side effects. The other compounds of this invention also cause similar results. In general, these compounds are ordinarily administered at dosage levels ranging from about 0.2 mg. to about 25 mg. per kg. of body weight per day, although variations will necessarily occur depending upon the condition and individual response of the subject being treated and the particular type of oral pharmaceutical formulation chosen.

The phenylguanidine compounds of this invention may be administered either alone or in combination with pharmaceutically acceptable carriers and such administration can be carried out in both single and multiple dosages. More particularly, the novel compounds of the invention can be administered in a wide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include solid diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted rat when tested therein for such purposes according to the procedure described by W. S. Hoffman, as reported in the *Journal of Biological Chemistry*, Vol. 120, p. 51 (1937). The latter method measures directly the amount of glucose in the blood at any given time and from this, the maximum percent decrease in blood sugar can be readily calculated. In this way, the present phenylguanidine final products are shown to markedly reduce the blood sugar levels of non-anesthetized, glucose-loaded rats when administered to them at dose levels as low as 50 mg./kg.

EXAMPLE 1

To a stirred, chilled (0°–5° C.) solution consisting of 3.08 g. (0.017 mole) of phenylisocyanide dichloride dissolved in 100 ml. of anhydrous diethyl ether, which was maintained under a dry nitrogen atmosphere, there was added during the course of a 30-minute period in a dropwise manner an ethereal solution consisting of 1.26 g. (0.017 mole) of freshly-distilled pyrrolidine and 1.79 g. (0.017 mole) of triethylamine dissolved in 50 ml. of anhydrous diethyl ether. The resulting suspension was then stirred at room temperature (~25° C.) for a period of one hour, filtered and the resulting filtrate treated dropwise with 1.65 g. (0.017 mole) of aniline dissolved in 50 ml. of diethyl ether. The final reaction mixture was then stirred vigorously at room temperature for a period of 18 hours and subsequently concentrated in vacuo to afford a residue, which was thereafter triturated with acetone to yield 3.02 g. (57%) of pure N,N'-diphenyl-1-pyrrolidinocarboxamidine hydrochloride, m.p. 288°–292° C. (decomp.). The analytical sample melted at 308°–310° C. (decomp.) after recrystallization from ethanol.

Anal. Calcd. for $C_{17}H_{19}N_3 \cdot HCl$: C, 67.65; H, 6.35; N, 13.92.

Found: C, 67.35; H, 6.57; N, 13.81.

EXAMPLE 2

The procedure described in Example 1 was repeated except that p-chloroaniline was the reagent employed instead of aniline in the second step of the reaction procedure, using the same molar proportions as before. In this particular case, the corresponding final product thus obtained was N-phenyl-N'-(p-chlorophenyl)-1-pyrrolidinocarboxamidine hydrochloride, m.p. 318°–319° C.

EXAMPLE 3

The procedure described in Example 1 was repeated except that 2,4-dichloroaniline was the reagent employed instead of aniline in the second step of the reaction procedure, using the same molar proportions as before. In this particular case, the corresponding final product thus obtained was N-phenyl-N'-(2,4-dichlorophenyl)-1-pyrrolidinocarboxamidine hydrochloride, m.p. 270°–271° C.

EXAMPLE 4

The procedure described in Example 1 was repeated except that N-methylaniline was the reagent employed instead of aniline in the second step of the reaction procedure, using the same molar proportions as before. In this particular case, the corresponding final product thus obtained was N-phenyl-N'-methyl-N'-phenyl-1-pyrrolidinocarboxamidine hydrochloride, m.p. 217°–218° C.

EXAMPLE 5

The procedure described in Example 1 was repeated except that 2-furfurylamine was the reagent employed instead of aniline in the second step of the reaction procedure, using the same molar proportions as before. In this particular case, the corresponding final product thus obtained was N-phenyl-N'-(2-furfuryl)-1-pyrrolidinocarboxamidine hydrochloride, m.p. 184°–186° C.

EXAMPLE 6

The procedure described in Example 1 was repeated except that 2-aminothiazole was the reagent employed instead of aniline in the second step of the reaction procedure, using the same molar proportions as before. In this particular case, the corresponding final product thus obtained was N-phenyl-N'-(2-thiazolyl)-1-pyrrolidinocarboxamidine hydrochloride, m.p. 150°–152° C.

EXAMPLE 7

The procedure described in Example 1 was repeated except that 2-aminopyridine was the reagent employed instead of aniline in the second step of the reaction procedure, using the same molar proportions as before. In this particular case, the corresponding final product thus obtained was N-phenyl-N'-(2-pyridyl)-1-pyrrolidinocarboxamidine hydrochloride, m.p. 154°–155° C.

EXAMPLE 8

To a stirred solution consisting of 13.50 g. (0.10 mole) of phenylisothiocyanate dissolved in 100 ml. of absolute ethanol at 10° C., there was added in one portion an alcoholic solution consisting of 7.10 g. (0.10 mole) of freshly-distilled pyrrolidine dissolved in 30 ml. of ethanol. The resulting suspension was then stirred at room temperature (~25° C.) for a period of one hour and filtered to ultimately afford 16.45 g. (80%) of pure 1-pyrrolidinothiocarboxanilide (m.p. 148°–149° C.) as the solid crystalline product.

A mixture consisting 17.45 g. (0.085 mole) of the above thiourea and 192 g. (1.36 mole) of methyl iodide in 500 ml. of methanol was then heated at the reflux point for a period of five hours while under a nitrogen atmosphere. The resulting solution was then concentrated in vacuo and the residue thereafter crystallized from methanol/diethyl ether to yield 27.74 g. (94%) of pure 2-methylthio-1-pyrrolidinocarboxanilide as the hydriodide salt, m.p. 160°–163° C.

A solution consisting of 12.0 g. (0.034 mole) of the above pseudothiourea salt and 7.3 g. (0.068 mole) of benzylamine dissolved in 100 ml. of tert.-butyl alcohol was slowly heated to 40° C. under a nitrogen atmosphere for a period of three days. Concentration of the reaction mixture (in vacuo) at the end of this time then gave an oily residue, which was subsequently crystallized from ethanol/diethyl ether to yield 11.76 g. (85%) of pure N-phenyl-N'-benzyl-1-pyrrolidinocarboxamidine hydriodide, m.p. 157° C.

EXAMPLE 9

The procedure described in Example 3 was repeated except that 2-imidazolinylamine was the appropriate organic amine of choice employed as reagent in place of benzylamine, using the same molar proportions as before. In this particular case, the corresponding final product obtained was N-phenyl-N'-(2-imidazolinyl)-1-pyrrolidinocarboxamidine hydriodide, m.p. 201°–202° C.

EXAMPLE 10

To a well-stirred suspension consisting of 3.50 g. (0.015 mole) of N-phenyl-N'-(3-pyridyl)thiourea in 100 ml. of methylene chloride, there was added a mixture consisting of 4.70 g. (0.018 mole) of triphenylphosphine, 2.28 g. (0.015 mole) of carbon tetrachloride and 1.52 g.

(0.015 mole) of triethylamine. The resulting solution was then refluxed for a period of 18 hours and finally concentrated in vacuo, followed by trituration of the newly-obtained residue with tert.-butyl alcohol. Suction filtration of the latter mixture then gave a clear filtrate, which was subsequently treated with 4.26 g. (0.060 mole) of pyrrolidine and thereafter heated at 50° C. for a period of 72 hours. At the end of this time, the spent reaction mixture was filtered and then treated with an excess of 10% aqueous hydrochloric acid. Concentration of the latter solution (in vacuo) then gave an oily residue, which was thereafter crystallized from ethanol/diethyl ether to yield 1.50 g. (29%) of pure N-phenyl-N'-(3-pyridyl)-1-pyrrolidinocarboxamidine in the form of the dihydrochloride salt (m.p. 330° C.).

EXAMPLE 11

Ten parts by weight of N,N'-diphenyl-1-pyrrolidinocarboxamidine hydrochloride (the product of Example 1) in 50 parts by volume of water are neutralized with 10 N aqueous sodium hydroxide solution. Extraction of the resulting aqueous solution with several portions of methylene chloride, followed by separation of the organic layer and its subsequent concentration under reduced pressure then affords N,N'-diphenyl-1-pyrrolidinocarboxamide as a free organic base compound.

In like manner, when any of the other phenylguanidine salts of this invention, like N-phenyl-N'-benzyl-1-pyrrolidinocarboxamidine hydriodide of Example 8, for instance, are each individually subjected to this same reaction procedure, the corresponding free organic base compound is the final product thus obtained.

EXAMPLE 12

The following phenylguanidine base compounds can be prepared by employing the procedures described in the previous Examples, starting from readily available materials in each instance:

N-(m-fluorophenyl)-N'-phenyl-1-pyrrolidinocarboxamidine
N-(p-chlorophenyl)-N'-phenyl-1-pyrrolidinocarboxamidine
N-(p-bromophenyl)-N'-phenyl-1-pyrrolidinocarboxamidine
N-(o-tolyl)-N'-phenyl-1-pyrrolidinocarboxamidine
N-(m-tolyl)-N'-phenyl-1-pyrrolidinocarboxamidine
N-(p-tolyl)-N'-phenyl-1-pyrrolidinocarboxamidine
N-(m-methoxyphenyl)-N'-phenyl-1-pyrrolidinocarboxamidine
N-(p-trifluoromethylphenyl)-N'-phenyl-1-pyrrolidinocarboxamidine
N-phenyl-N'-(p-fluorophenyl)-1-pyrrolidinocarboxamidine
N-phenyl-N'-(o-bromophenyl)-1-pyrrolidinocarboxamidine
N-phenyl-N'-(m-tolyl)-1-pyrrolidinocarboxamidine
N-phenyl-N'-(o-ethylphenyl)-1-pyrrolidinocarboxamidine
N-phenyl-N'-(2,4-dimethylphenyl)-1-pyrrolidinocarboxamidine
N-phenyl-N'-(o-anisyl)-1-pyrrolidinocarboxamidine
N-phenyl-N'-(m-trifluomethylphenyl)-1-pyrrolidinocarboxamidine
N-(p-tolyl)-N'-(2,4-dichlorophenyl)-1-pyrrolidinocarboxamidine
N-phenyl-N'-(n-butyl)-N'-phenyl-1-pyrrolidinocarboxamidine
N-phenyl-N'-methyl-N'-(p-chlorophenyl)-1-pyrrolidinocarboxamidine
N-phenyl-N'-(δ-phenyl-n-butyl)-1-pyrrolidinocarboxamidine
N-(p-chlorophenyl)-N'-(β-phenylethyl)-1-pyrrolidinocarboxamidine
N,N'-diphenyl-1-piperidinocarboxamidine
N,N'-diphenyl-1-homopiperidinocarboxamidine
N,N'-diphenyl-1-morpholinocarboxamidine
N-phenyl-N'-(p-chlorophenyl)-1-morpholinocarboxamidine
N-phenyl-N'-(2,4-dichlorophenyl)-1-morpholinocarboxamidine
N-phenyl-N'-benzyl-1-morpholinocarboxamidine
N,N'-diphenyl-1-thiomorpholinocarboxamidine
N,N'-diphenyl-1-piperazinocarboxamidine
N,N'-diphenyl-1-(N-methylpiperazino)carboxamidine
N,N'-diphenyl-1-(N-benzylpiperazino)carboxamidine
N,N'-diphenyl-1-(N-phenylpiperazino)carboxamidine
N,N'-diphenyl-N",N"-dimethylguanidine
N-phenyl-N'-(p-chlorophenyl)-N",N"-di(n-butyl)-guanidine
N-(m-fluorophenyl)-N'-(2-pyridyl)-1-pyrrolidinocarboxamidine
N-(p-chlorophenyl)-N'-(3-pyridyl)-1-pyrrolidinocarboxamidine
N-(p-bromophenyl)-N'-(4-pyridyl)-1-pyrrolidinocarboxamidine
N-(o-tolyl)-N'-(3-pyridyl)-1-pyrrolidinocarboxamidine
N-(m-methoxyphenyl)-N'-(2-pyridyl)-1-pyrrolidinocarboxamidine
N-(p-trifluoromethylphenyl)-N'-(3-pyridyl)-1-pyrrolidinocarboxamidine
N-phenyl-N'-(n-butyl)-N'-(4-pyridyl)-1-pyrrolidinocarboxamidine
N-phenyl-N'-methyl-N'-(3-pyridyl)-1-pyrrolidinocarboxamidine
N-phenyl-N'-(2-picolinyl)-1-pyrrolidinocarboxamidine
N-(p-chlorophenyl)-N'-δ-(3-pyridyl)butyl-1-pyrrolidinocarboxamidine
N-phenyl-N'-(4-pyridyl)-1-piperidinocarboxamidine
N-phenyl-N'-(3-pyridyl)-1-homopiperidinocarboxamidine
N-phenyl-N'-(2-pyridyl)-1-morpholinocarboxamidine
N-phenyl-N'-(3-pyridyl)-1-morpholinocarboxamidine
N-phenyl-N'-methyl-N'-(4-pyridyl)-1-morpholinocarboxamidine
N-phenyl-N'-(3-picolinyl)-1-morpholinocarboxamidine
N-phenyl-N'-(2-pyridyl)-1-thiomorpholinocarboxamidine
N-phenyl-N'-(3-pyridyl)-1-piperazinocarboxamidine
N-phenyl-N'-(4-pyridyl)-1-(N-methylpiperazino)carboxamidine
N-phenyl-N'-(3-pyridyl)-1-(N-benzylpiperazino)carboxamidine
N-phenyl-N'-(2-pyridyl)-1-(N-phenylpiperazino)carboxamidine
N-phenyl-N'-(3-pyridyl)-N",N"-dimethylguanidine
N-phenyl-N'-(4-pyridyl)-N",N"-di(n-butyl)guanidine
N-(m-fluorophenyl)-N'-(2-furfuryl)-1-pyrrolidinocarboxamidine
N-(p-chlorophenyl)-N'-(3-furfuryl)-1-pyrrolidinocarboxamidine
N-(p-bromophenyl)-N'-(2-thenyl)-1-pyrrolidinocarboxamidine
N-(m-tolyl)-N'-(3-thenyl)-1-pyrrolidinocarboxamidine
N-(m-methoxyphenyl)-N'-(2-furfuryl)-1-pyrrolidinocarboxamidine N-(p-trifluoromethylphenyl)-N'-(3-thenyl)-1-pyrrolidinocarboxamidine
N-phenyl-N'-(n-butyl)-N'-(2-thenyl)-1-pyrrolidinocarboxamidine
N-phenyl-N'-methyl-N'-(3-furfuryl)-1-pyrrolidinocarboxamidine
N-phenyl-N'-γ-(3-furyl)propyl-1-pyrrolidinocarboxamidine
N-(p-chlorophenyl)-N'-β-(2-thienyl)ethyl-1-pyrrolidinocarboxamidine
N-phenyl-N'-(2-furfuryl)-1-piperidinocarboxamidine
N-phenyl-N'-(3-thenyl)-1-homopiperidinocarboxamidine
N-phenyl-N'-(2-thenyl)-1-morpholinocarboxamidine
N-phenyl-N'-(3-furfuryl)-1-morpholinocarboxamidine
N-phenyl-N'-(2-furfuryl)-1-thiomorpholinocarboxamidine
N-phenyl-N'-(2-thenyl)-1-(N-methylpiperazino)carboxamidine
N-phenyl-N'-(2-furfuryl)-1-(N-phenylpiperazino)carboxamidine
N-phenyl-N'-(3-thenyl)-N'',N''-dimethylguanidine
N-phenyl-N'-(2-furfuryl)-N'',N''-di(n-propyl)guanidine
N-(m-fluorophenyl)-N'-(2-thiazolyl)-1-pyrrolidinocarboxamidine
N-(p-chlorophenyl)-N'-(2-imidazolyl)-1-pyrrolidinocarboxamidine
N-(p-tolyl)-N'-(2-imidazolinyl)-1-pyrrolidinocarboxamidine
N-(m-methoxyphenyl)-N'-(2-thiazolyl)-1-pyrrolidinocarboxamidine
N-(p-rifluoromethylphenyl)-N'-(2-imidazolyl)-1-pyrrolidinocarboxamidine
N-(phenyl)-N'-(n-butyl)-N'-(2-imidazolinyl)-1-pyrrolidinocarboxamidine
N-phenyl-N'-methyl-N'-(2-thiazolyl)-1-pyrrolidinocarboxamidine
N-phenyl-N'-(2-imidazolinylmethyl)-1-pyrrolidinocarboxamidine
N-phenyl-N'-δ-(2-thiazolyl)butyl-1-pyrrolidinocarboxamidine
N-phenyl-N'-(2-imidazolyl)-1-piperidinocarboxamidine
N-phenyl-N'-(2-imidazolinyl)-1-homopiperidinocarboxamidine
N-phenyl-N'-(2-thiazolyl)-1-morpholinocarboxamidine
N-phenyl-N'-(2-imidazolyl)-1-morpholinocarboxamidine
N-phenyl-N'-(2-imidazolinyl)-1-thiomorpholinecarboxamidine
N-phenyl-N'-(2-thiazolyl)-1-piperazinocarboxamidine
N-phenyl-N'-(2-imidazolyl)-1-(N-methylpiperazino)carboxamidine
N-phenyl-N'-(2-imidazolinyl)-1-(N-phenylpiperazino)carboxamidine
N-phenyl-N'(2-thiazolyl)-N'',N''-dimethylguanidine
N-phenyl-N'-(2-imidazolyl)-N'',N''-di(n-butyl)guanidine
N-phenyl-N'-(2-imidazolinyl)-N'',N''-diethylguanidine

EXAMPLE 13

The non-toxic hydrohalide acid addition salts of each of the previously reported phenylguanidine base compounds of this invention, such as the corresponding hydrochloride, hydrobromide and hydriodide salts, are each individually prepared by first dissolving the respective organic base compound in absolute ether followed by the introduction of the appropriate hydrohalide gas into the reaction solution until saturation of same is complete with respect to said gas, whereupon the desired acid addition salt soon precipitates from said solution. In this way, 1.0 g. of N,N'-diphenyl-1-pyrrolidinocarboxamidine, obtained as a free base product in Example 11 is converted via dry hydrogen bromide gas to the corresponding hydrobromide acid addition salt in substantially quantitative yield.

EXAMPLE 14

The nitrate, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts of each of the aforementioned phenylguanidine base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition therefrom. In this manner, equimolar amounts of N-phenyl-N'-benzyl-1'-pyrrolidinocarboxamidine and concentrated sulfuric acid react to afford the corresponding sulfuric acid addition salt. In like manner, each of the other salts is similarly prepared.

EXAMPLE 15

A dry solid pharmaceutical composition is prepared by blending the following materials together in the proportions by weight specified below:

| | |
|---|---|
| N-phenyl-N'-methyl-N'-phenyl-1-pyrrolidinocarboxamidine hydrochloride | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each table being of such size that it contains 200 mg. of the active ingredient. Other tablets are also prepared in a similar fashion containing 25, 50 and 100 mg. of the active ingredient, respectively, by merely using the appropriate amount of the phenylguanidine salt in each case.

EXAMPLE 16

A dry solid pharmaceutical composition is prepared by combining the following materials together in the proportions by weight indicated:

| | |
|---|---|
| N-phenyl-N'-(p-chlorophenyl)-1-pyrrolidinocarboxamidine hydrochloride | 50 |
| Calcium carbonate | 20 |
| Polyethylene glycol, average molecular weight 4000 | 30 |

The dried mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE 17

The following phenylguanidine final products of Examples 1-9, respectively, were tested for hypoglycemic activity in terms of their ability to exhibit improved glucose tolerance in groups of five or six male albino rats (each weighing approximately 200-225 g.) of the Charles River strain. No anesthetic was used in this study. The rats were fasted for approximately 18-24 hours prior to administration, a blood sample (zero time) was taken from the tail vein of each animal (having cut at a point just 2 mm. from the tip of the tail) and each animal so examined was thereafter treated with glucose at a dose level of 1.0 g./kg. (made up in 0.9% saline), via the intraperitoneal route of administration, followed by treatment with either saline alone (controls) or the test compound to be administered at a dose level of 50 mg./kg., also by the intraperitoneal route of administration. Additional blood samples were then taken from the tail vein in the same manner as before at a one-hour interval after administration of both the glucose and the compound. The samples were immediately diluted 1:10 (by volume) with 0.1% heparin in 0.9% saline. Blood glucose concentrations (mg./dl.) were then determined by adapting the method of W. S. Hoffman [*Journal of Biological Chemistry*, Vol. 120, p. 51 (1937)] to the Autoanalyzer instrument produced by Technicon Instruments Corporation of Chauncey, N.Y. On this basis, the difference (or decrease) in percent blood glucose compared to controls was calculated (at one hour post-administration of both the glucose and the compound) and reported as such (i.e., as hypoglycemic activity in terms of improved glucose tolerance) for the various compounds listed in the table below:

| Compound | Blood Glucose % Decrease |
| --- | --- |
| Product of Example 1 | 45 |
| Product of Example 2 | 48 |
| Product of Example 3 | 40 |
| Product of Example 4 | 53 |
| Product of Example 5 | 28 |
| Product of Example 6 | 15 |
| Product of Example 7 | 21 |
| Product of Example 8 | 39 |
| Product of Example 9 | 10 |

I claim:

1. A compound selected from the group consisting of phenylguanidine bases of the formula:

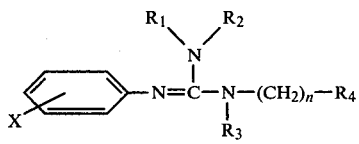

and the pharmaceutically acceptable acid addition salts thereof, wherein

X is a member selected from the group consisting of hydrogen, fluorine, chlorine, bromine, trifluoromethyl, lower alkyl and lower alkoxy;

$R_1$ and $R_2$, when taken separately, are each lower alkyl, and when taken together complete a pyrrolidino ring;

$R_3$ is hydrogen or lower alkyl;

$R_4$ is a member selected from the group consisting of pyridyl, furyl and thienyl; and n is an integer of from zero to four, inclusive.

2. A compound as claimed in claim 1 wherein X is hydrogen, $R_1$ and $R_2$ when taken together complete a pyrrolidine ring, $R_3$ is hydrogen, $R_4$ is pyridyl and n is zero.

3. A compound as claimed in claim 1 wherein X is hydrogen, $R_1$ and $R_2$ when taken together complete a pyrrolidine ring, $R_3$ is hydrogen, $R_4$ is furyl and n is one.

4. A pharmaceutical composition suitable for oral administration comprising a pharmaceutically acceptable carrier and an effective blood sugar lowering amount of a compound as claimed in claim 1.

5. A method for lowering blood sugar in the treatment of a diabetic host, which comprises orally administering to said host an effective blood sugar lowering amount of a compound as claimed in claim 1.

* * * * *